(12) United States Patent
Haider

(10) Patent No.: US 9,662,254 B2
(45) Date of Patent: May 30, 2017

(54) PATIENT TRANSPORTATION SYSTEM

(71) Applicant: Sultan Haider, Erlangen (DE)

(72) Inventor: Sultan Haider, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 14/750,306

(22) Filed: Jun. 25, 2015

(65) Prior Publication Data

US 2015/0374567 A1 Dec. 31, 2015

(30) Foreign Application Priority Data

Jun. 25, 2014 (DE) ......................... 10 2014 212 202

(51) Int. Cl.
 *A61G 7/00* (2006.01)
 *A61G 7/08* (2006.01)
 *A61B 6/04* (2006.01)
 *A61G 7/05* (2006.01)

(52) U.S. Cl.
 CPC .............. *A61G 7/08* (2013.01); *A61B 6/0407* (2013.01); *A61G 7/05* (2013.01); *A61G 7/0528* (2016.11); *A61G 2203/10* (2013.01)

(58) Field of Classification Search
 CPC . A61G 7/00; A61G 7/08; A61G 7/012; A61G 7/018; A61G 7/10–7/1011
 See application file for complete search history.

(56) References Cited

U.S. PATENT DOCUMENTS

| 5,083,625 | A | * | 1/1992 | Bleicher | ................ | B62D 61/10 |
| | | | | | | 180/202 |
| 5,580,207 | A | | 12/1996 | Kiebooms et al. | | |
| 6,877,572 | B2 | * | 4/2005 | Vogel | ....................... | A61G 7/00 |
| | | | | | | 180/15 |
| 7,419,019 | B1 | * | 9/2008 | White | ..................... | A61G 7/08 |
| | | | | | | 180/19.1 |
| 2011/0083274 | A1 | | 4/2011 | Newkirk et al. | | |
| 2011/0087416 | A1 | | 4/2011 | Patmore | | |
| 2011/0173752 | A1 | | 7/2011 | Weiler | | |
| 2014/0331406 | A1 | | 11/2014 | Haider et al. | | |

FOREIGN PATENT DOCUMENTS

| DE | 9420429 U1 | 3/1995 |
| DE | 102010005015 A1 | 7/2011 |
| DE | 102012213202 A1 | 1/2014 |
| DE | 102013208610 A1 | 11/2014 |
| EP | 1985275 A2 | 10/2008 |

OTHER PUBLICATIONS

German Office action for related German Application No. 10 2014 212 202.3, dated Feb. 20, 2015, with English Translation.

* cited by examiner

*Primary Examiner* — Erez Gurari
(74) *Attorney, Agent, or Firm* — Lempia Summerfield Katz LLC

(57) ABSTRACT

A patient transportation system includes a patient transportation apparatus. The patient transportation apparatus is configured for docking to a medical device and includes a plurality of wheels. The patient transportation apparatus also includes a handle unit that may be moved in a plurality of positions for controlling the patient transportation apparatus. The patient transportation apparatus also includes a coupling unit for connecting the plurality of wheels to the handle unit and for changing a wheel position of at least one wheel of the plurality of wheels in accordance with a position of the movable handle unit.

12 Claims, 2 Drawing Sheets

PATIENT TRANSPORTATION SYSTEM

This application claims the benefit of DE 10 2014 212 202.3, filed on Jun. 25, 2014, which is hereby incorporated by reference in its entirety.

BACKGROUND

The present embodiments relate to a patient transportation system.

In hospitals, patients are transported inside various examination devices or between locations and examination rooms. Because of the health status of the patient, the patient is frequently transported lying on a patient table. Typically, for an examination with an examination device (e.g., magnetic resonance device, computed tomography device, X-ray device, radiotherapy device, etc.), the patient is to be transported from a location to a place provided for the examination process, mostly inside the examination device.

SUMMARY AND DESCRIPTION

The scope of the present invention is defined solely by the appended claims and is not affected to any degree by the statements within this summary.

The present embodiments may obviate one or more of the drawbacks or limitations in the related art. For example, assistance is provided for the operating personnel while patients are being transported.

A patient transportation system is provided. The patient transportation system includes a patient transportation apparatus configured for docking to a medical device. The patient transportation apparatus includes a plurality of wheels, a handle unit that may be moved in a plurality of positions for controlling the patient transportation apparatus, and a coupling unit for connecting the wheels to the handle unit and for changing a wheel position of at least one wheel of the plurality of wheels in accordance with a position of the movable handle unit.

One embodiment of the patient transportation system includes a patient transportation apparatus (e.g., a trolley) having a plurality of wheels (e.g., at least four; five) that is configured for docking to a medical device or a medical modality (e.g., computer tomograph, nuclear spin tomograph, x-ray device, radiation therapy device, etc.).

The patient transportation system includes a handle unit that may be moved in a plurality of positions for controlling the patient transportation apparatus. In such cases, the term handle unit, for example, may not exclusively be a rod, a lever or a guide rail, with which the patient transportation apparatus may be controlled and/or advanced.

The patient transportation system includes a coupling unit for connecting the wheels to the handle unit and for changing a wheel position of at least one wheel of the plurality of wheels in accordance with a position of the movable handle unit. The change in the wheel position may relate to a change in direction but may also relate to a blocking of a wheel for a braking of the patient transportation apparatus.

The patient transportation system may be the same as the patient transportation apparatus.

It is not only the docking process itself that may be assisted but instead also the approach of the patient transportation apparatus to the docking interface of the medical device. One or more of the present embodiments assist operating personnel with transporting the transportation apparatus to the interface provided for the docking process and thus further facilitate transportation and docking for medical examinations or treatments. The patient transportation apparatus may be actively controlled by a user, such as, for example, nursing staff, with respect to direction and speed.

One or more of the present embodiments use, for example, a coupling unit to connect the wheels to the handle unit and to change a wheel position of at least one wheel of the plurality of wheels in accordance with a position of the movable handle unit in order thus to facilitate both transportation and also the docking of the patient transportation apparatus.

In an embodiment, the patient transportation apparatus includes a centrally arranged wheel that is generally arranged centrally between the other wheels, and the wheel position of the central wheel is controlled by the handle unit in order thus to enable easier control. It is not only more efficient control around a vertical axis of the patient transportation apparatus that is achieved but also efficient control along a lateral direction.

In an advantageous embodiment, the central wheel is coupled to one or a number of other wheels of the plurality of wheels, and the wheel positions of the coupled wheels may be adjusted in accordance with the wheel position of the central wheel. The wheel position of the central wheel may be adjusted by the handle unit and the coupling unit. As a result, the wheel position may also be easily adjusted during the transportation process even with one hand.

In a further embodiment, the patient transportation apparatus includes a plurality of central wheels. These may be selectively coupled to other wheels in order thus to enable improved control. These may, however, also provide for a simple control if another central wheel is no longer to be functional.

In one embodiment, the patient transportation system includes a motor that interacts with the coupling unit in order to change the at least one wheel position. This motor may also be configured to drive the wheels and/or to adjust the height of the patient support. One or two separate motors may alternatively also be provided for the latter functions. This facilitates easier actuation of the coupling unit.

In an advantageous embodiment, the motor is configured to drive the wheels and/or to adjust the height of a patient support. The advance of the patient transportation apparatus is as a result also assisted, and the strain on a user of the patient transportation apparatus is reduced.

In a further embodiment, the handle unit is movably mounted on at least one rail. Further degrees of freedom are as a result achieved (e.g., directions along which the handle unit may be moved). A number of possibilities of changing a wheel position are thus also created.

In one embodiment, a position of the movable handle unit is configured for docking to the medical device. The patient transportation apparatus may thus be fixed to the medical device in order thus to facilitate the moving of a patient to another bed.

In the context of the present embodiments, a medical device with a patient transportation system is also provided.

The advantages of the medical device essentially correspond to the advantages of the patient transportation system, which are explained above in detail. Features, advantages or alternative embodiments mentioned herein are also to be applied to the other subject matter, and vice versa. In other words, the claims that are directed toward a patient transportation apparatus, for example, may also be developed with the features described or claimed in connection with a medical device.

DETAILED DESCRIPTION

Figure 1:
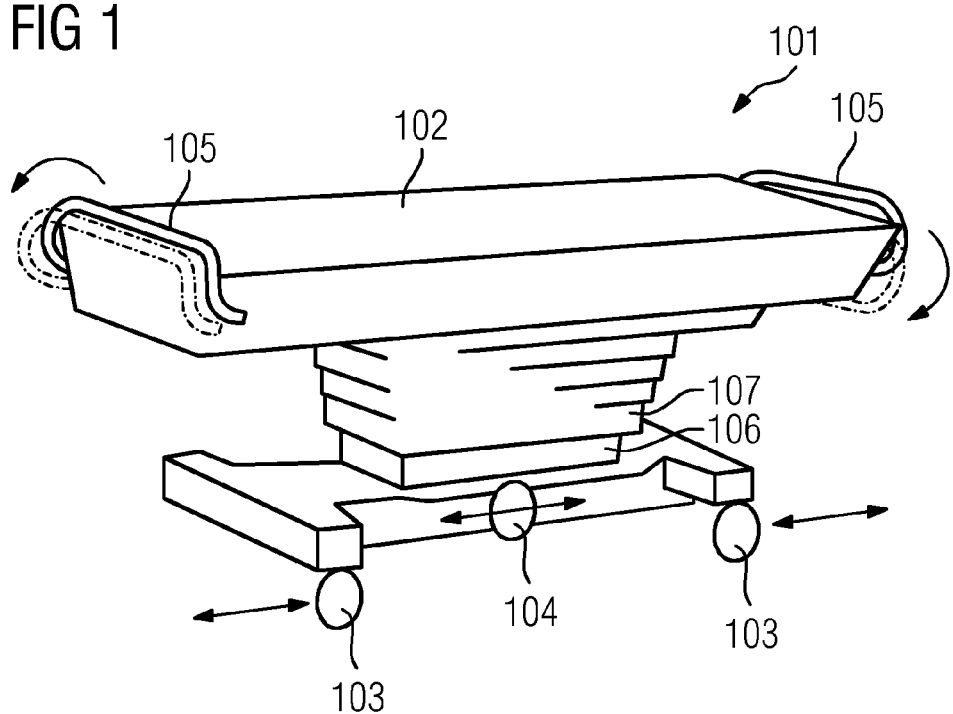
FIG. 1 shows a first embodiment of a patient transportation system.

FIG. 1 shows one embodiment of a patient transportation system 101. The patient transportation system 101 includes a patient transportation apparatus configured for docking to a medical device and including five wheels 103, 104 (of which three are visible in the Figure shown), a handle unit 105 that may be moved in a plurality of positions for controlling the patient transportation apparatus 102, and a coupling unit 106 for connecting the wheels 103, 104 to the handle unit 105 and for changing a wheel position of at least one wheel from a number of wheels 103, 104 in accordance with a position of the movable handle unit 105.

The patient transportation system 101 shown in FIG. 1 shows two handle units 105, one on a front region of the patient transportation apparatus 102 and one on an end region of the patient transportation apparatus 102. The handle units 105 may be operated by a user, such as, for example, nursing staff in a hospital.

In such cases, the patient transportation apparatus 102 includes a centrally arranged wheel 104 that may be controlled by the handle unit 105. In such cases, the centrally arranged wheel 104 is also coupled to one or a number of the other wheels 103, and the wheel positions of the coupled wheels 103 may be adjusted in accordance with the wheel position of the central wheel 104. The central wheel 104 may be arranged centrally between the other wheels 103. The other wheels are arranged on edge regions of the patient transportation apparatus 102. In one embodiment, the patient transportation apparatus 102 may include a plurality of central wheels 104.

The patient transportation system 101 is also equipped, for example, with a motor 107 that is configured for driving the wheels 103, 104 and/or for adjusting the height of a patient support.

By moving the handle unit 105 in the arrow directions of the handle unit 105 shown in FIG. 1, the example shows how a movement of the wheels 103, 104 in the arrow direction of the wheels 103, 104 (e.g., a movement in a longitudinal direction of the patient transportation apparatus 102) is enabled.

Figure 2:
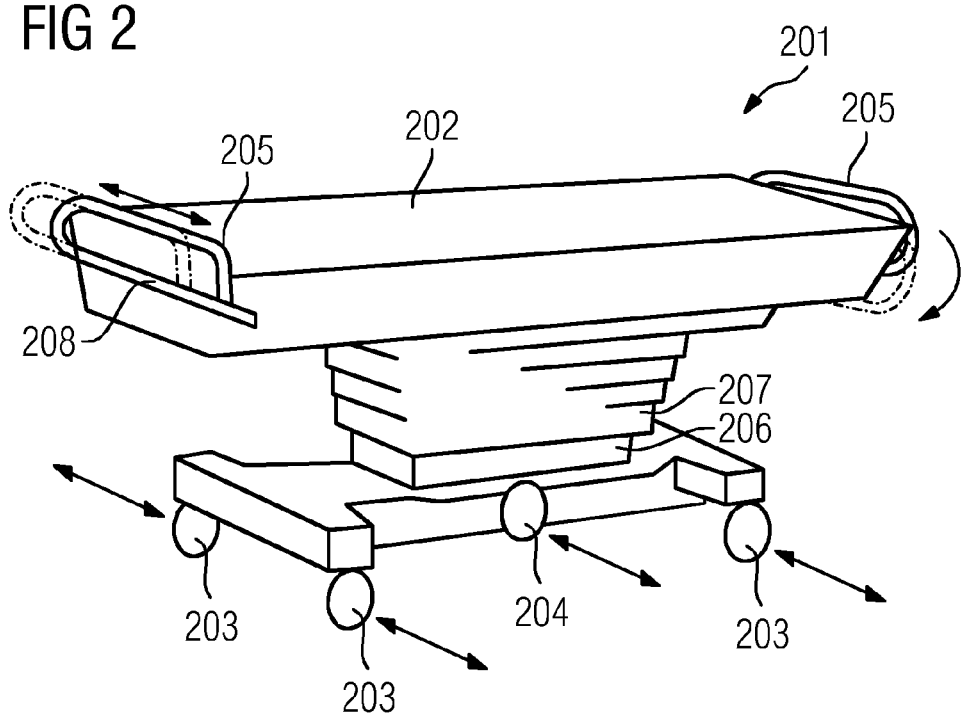
FIG. 2 shows a second embodiment of a patient transportation system.
Figure 3:
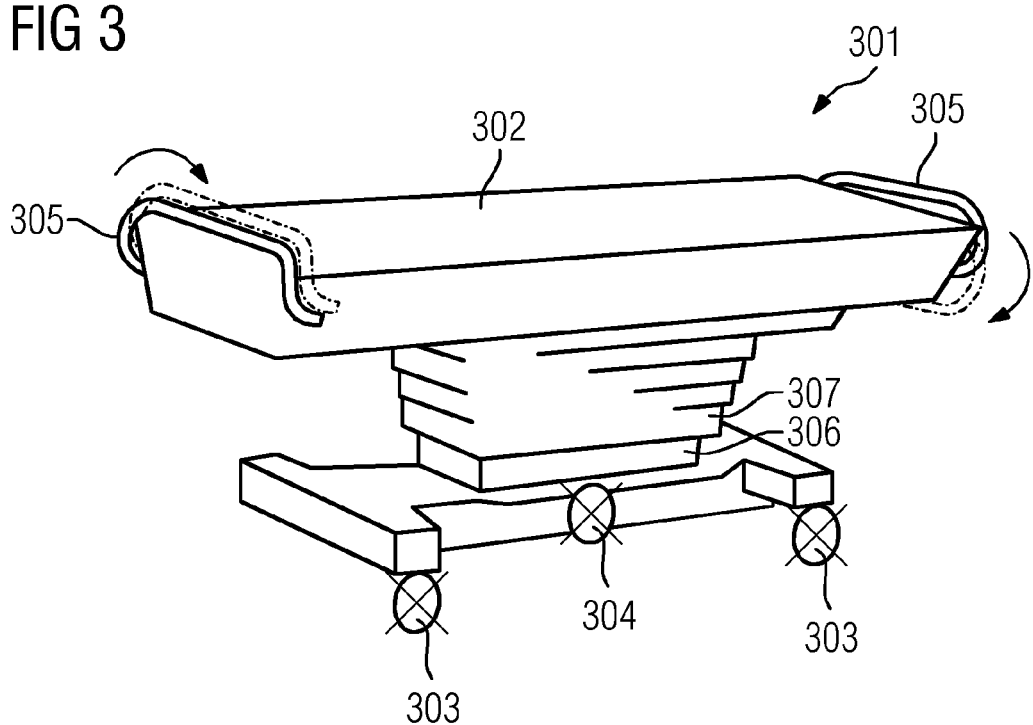
FIG. 3 shows a third embodiment of a patient transportation system.
Figure 4:
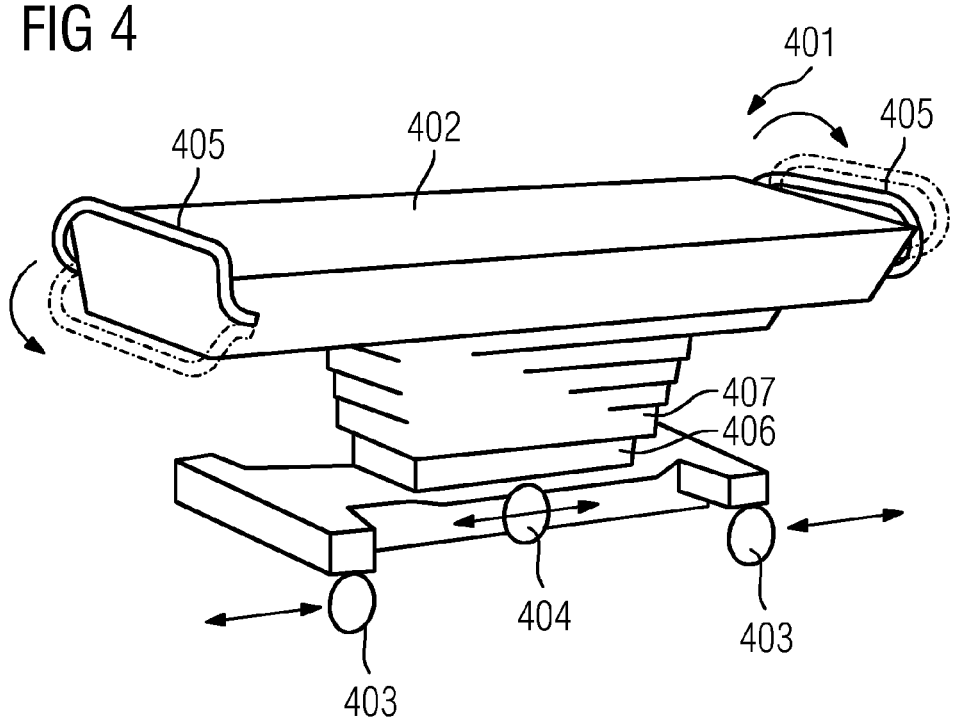
FIG. 4 shows a fourth embodiment of a patient transportation system

FIG. 2 to FIG. 4 show alternative exemplary embodiments of a patient transportation system 101, 201, 301, 401 from FIG. 1. The following descriptions are essentially restricted to the differences from the exemplary embodiment in FIG. 1, where with regard to components, features and functions that remain the same, reference is made to the description of the exemplary embodiment in FIG. 1.

FIG. 2 shows a further embodiment of a patient transportation system 201. The handle unit 205 of the patient transportation system 201 is moveably mounted, for example, on a rail 208. A position of the movable handle unit 105, 205 is configured for docking to the medical device.

By moving the handle unit 205 in the arrow directions of the handle unit 205 shown in FIG. 1, the example shows how a movement of the wheels 203, 204 in the arrow direction of the wheels 203, 204 (e.g., a movement in a direction at right angles to the longitudinal direction of the patient transportation apparatus 202) is enabled.

FIG. 3 shows a third embodiment of a patient transportation system 301.

By moving the handle unit 305 in the arrow directions of the handle unit 305 shown in FIG. 1, a blocking of the wheels 303, 304 is achieved in the example shown.

FIG. 4 shows a fourth embodiment of a patient transportation system 401.

By moving the handle unit 405 in the arrow directions of the handle unit 405 shown in FIG. 1, the example shows how a movement of the wheels 403, 404 in the arrow direction of the wheels 403, 404 (e.g., a movement in a longitudinal direction of the patient transportation apparatus 402) is enabled. A docking to a medical device is also enabled.

The movements of the handle unit 105, 205, 305, 405 in FIG. 1 to FIG. 4 are shown by way of example for the control of the patient transportation apparatus 102, 202, 302, 402 and may also be interchanged with one another. The movement of the handle unit 105, 205, 305, 405, which results in a blocking of the wheels 103, 104, 203, 204, 303, 304, 403, 404, may in another example be configured to advance the patient transportation apparatus 102, 202, 302, 402 in a longitudinal direction of the patient transportation apparatus 102, 202, 302, 402, and vice versa.

Although the invention has been illustrated and described in greater detail based on the exemplary embodiments, the invention is not limited by the disclosed examples. Other variations may be derived herefrom by the person skilled in the art without departing from the scope of protection of the invention.

One or more of the present embodiments relate to a patient transportation system. The patient transportation system includes a patient transportation apparatus configured for docking to a medical device. The patient transportation apparatus includes a plurality of wheels, a handle unit that may be moved in a plurality of positions for controlling the patient transportation apparatus, and a coupling unit for connecting the wheels to the handle unit and for changing a wheel position of at least one wheel of the plurality of wheels in accordance with a position of the movable handle unit. In an advantageous embodiment, the patient transportation apparatus includes a centrally arranged wheel, and the wheel position of the central wheel is controlled by the handle unit.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A patient transportation system comprising:
a patient transportation apparatus configured for docking to a medical device and comprising a plurality of wheels;
a handle unit that is moveably mounted on at least one rail and movable in a plurality of positions for controlling the patient transportation apparatus, movement of the plurality of wheels in a direction being enabled when the handle unit is moved from a first position of the plurality of positions to a second position of the plurality of positions; and
a coupling unit for connecting the plurality of wheels to the handle unit and for changing a wheel position of at least one wheel of the plurality of wheels in accordance with a position of the movable handle unit,
wherein the at least one wheel comprises a centrally arranged wheel, and
wherein a wheel position of the centrally arranged wheel is controlled by the moveable handle unit, such that the centrally arranged wheel is moveable from a first wheel position to a second wheel position in accordance with the position of the movable handle unit, the first wheel position of the centrally arranged wheel and the second wheel position of the centrally arranged wheel defining a first direction and a second direction, respectively, in which the centrally arranged wheel and the patient transportation apparatus are moveable, the second direction being at an angle relative to the first direction.

2. The patient transportation system of claim 1, wherein the centrally arranged wheel is coupled to one or a number of the other wheels of the plurality of wheels, and
wherein wheel positions of the coupled wheels are adjustable in accordance with the wheel position of the central wheel.

3. The patient transportation system of claim 1, wherein the plurality of wheels comprises a plurality of central wheels.

4. The patient transportation system of claim 1, further comprising a motor that interacts with the coupling unit to change the wheel position.

5. The patient transportation system of claim 4, wherein the motor is configured to drive the plurality of wheels, adjust a height of a patient support, or drive the plurality of wheels and adjust the height of the patient support.

6. The patient transportation system of claim 1, wherein a position of the movable handle unit is configured for docking to the medical device.

7. A medical device comprising:
a patient transportation system comprising:
a patient transportation apparatus configured for docking to a medical device and comprising a plurality of wheels;
a handle unit that is moveably mounted on at least one rail and movable in a plurality of positions for controlling the patient transportation apparatus, movement of the plurality of wheels in a direction being enabled when the handle unit is moved from a first position of the plurality of positions to a second position of the plurality of positions; and
a coupling unit for connecting the plurality of wheels to the handle unit and for changing a wheel position of at least one wheel of the plurality of wheels in accordance with a position of the movable handle unit,
wherein the at least one wheel comprises a centrally arranged wheel, and
wherein a wheel position of the centrally arranged wheel is controlled by the movable handle unit, such that the centrally arranged wheel is moveable from a first wheel position to a second wheel position in accordance with the position of the movable handle unit, the first wheel position of the centrally arranged wheel and the second wheel position of the centrally arranged wheel defining a first direction and a second direction, respectively, in which the centrally arranged wheel and the patient transportation apparatus are moveable, the second direction being at an angle relative to the first direction.

8. The medical device of claim 7, wherein the centrally arranged wheel is coupled to one or a number of the other wheels of the plurality of wheels, and
wherein wheel positions of the coupled wheels are adjustable in accordance with the wheel position of the central wheel.

9. The medical device of claim 7, wherein the plurality of wheels comprises a plurality of central wheels.

10. The medical device of claim 7, wherein the patient transportation system further comprises a motor that interacts with the coupling unit to change the wheel position.

11. The medical device of claim 10, wherein the motor is configured to drive the plurality of wheels, to adjust a height of a patient support, or to drive the plurality of wheels and adjust the height of the patient support.

12. The medical device of claim 7, wherein a position of the movable handle unit is configured for docking to the medical device.

* * * * *